(12) United States Patent
Xu

(10) Patent No.: US 10,694,971 B2
(45) Date of Patent: Jun. 30, 2020

(54) RECONFIGURABLE SENSOR CIRCUIT

(71) Applicant: Stichting IMEC Nederland, AE Eindhoven (NL)

(72) Inventor: Jiawei Xu, Leuven (BE)

(73) Assignee: Stichting IMEC Nederland, AE Eindhoven (NL)

( * ) Notice: Subject to any disclaimer, the term of this patent is extended or adjusted under 35 U.S.C. 154(b) by 276 days.

(21) Appl. No.: 15/689,930

(22) Filed: Aug. 29, 2017

(65) Prior Publication Data

US 2018/0055409 A1 Mar. 1, 2018

(30) Foreign Application Priority Data

Aug. 30, 2016 (EP) .................................... 16186375

(51) Int. Cl.
*A61B 5/05* (2006.01)
*A61B 5/053* (2006.01)
(Continued)

(52) U.S. Cl.
CPC ........ *A61B 5/0531* (2013.01); *A61B 5/04004* (2013.01); *A61B 5/6804* (2013.01);
(Continued)

(58) Field of Classification Search
CPC ... A61B 5/0531; A61B 5/0533; A61B 5/0478; A61B 5/0408; A61B 5/6804;
(Continued)

(56) References Cited

U.S. PATENT DOCUMENTS

| 5,281,860 A | 1/1994 | Krenik et al. | |
|---|---|---|---|
| 2003/0106989 A1* | 6/2003 | Bloehbaum | H03F 3/08 250/214 A |

(Continued)

FOREIGN PATENT DOCUMENTS

| EP | 2173031 A1 | 4/2010 |
|---|---|---|
| EP | 2893873 A2 | 7/2015 |

(Continued)

OTHER PUBLICATIONS

Zhang et al., "Characterization of a Configurable Sensor Signal Conditioning Circuit for Multi-Sensor Microsystems", IEEE Sensors, pp. 198-201, 2004.

(Continued)

*Primary Examiner* — Christian Jang
(74) *Attorney, Agent, or Firm* — Moser Taboada

(57) ABSTRACT

According to an aspect of the present inventive concept there is provided a reconfigurable sensor circuit comprising: an input stage including a first input terminal and a second input terminal, and
an amplification stage including:
a first amplifier having a non-inverting input, an inverting input and an output connected to the inverting input of the first amplifier via a first resistor,
a second amplifier having a non-inverting input, an inverting input and an output connected to the inverting input of the second amplifier via a second resistor, and
first switching circuitry adapted to be arranged in a first state, wherein the amplification stage is in a differential amplifier configuration, and in a second state, wherein the amplification stage is in a transimpedance amplifier configuration,
wherein, in the differential amplifier configuration, the first amplifier and the second amplifier are together
(Continued)

configured as a differential amplifier connected to the first and the second input terminals, and wherein, in the transimpedance amplifier configuration, at least the first amplifier is configured as a transimpedance amplifier connected to the first input terminal.

14 Claims, 4 Drawing Sheets

(51) Int. Cl.
    *A61B 5/00*     (2006.01)
    *H03F 3/45*     (2006.01)
    *A61B 5/04*     (2006.01)
    *A61B 5/0408*     (2006.01)
    *A61B 5/0478*     (2006.01)

(52) U.S. Cl.
    CPC ........... *H03F 3/45* (2013.01); *H03F 3/45475* (2013.01); *A61B 5/0408* (2013.01); *A61B 5/0478* (2013.01); *A61B 5/0533* (2013.01); *H03F 2200/165* (2013.01); *H03F 2200/411* (2013.01); *H03F 2203/45138* (2013.01); *H03F 2203/45288* (2013.01)

(58) Field of Classification Search
    CPC ............. A61B 5/04004; H03F 3/45475; H03F 2203/45288; H03F 2200/411; H03F 2200/165; H03F 3/45; H03F 2203/45138
    See application file for complete search history.

(56) References Cited

U.S. PATENT DOCUMENTS

| | | | |
|---|---|---|---|
| 2004/0130397 A1* | 7/2004 | Mactaggart | ............... H03F 3/08 330/308 |
| 2007/0120044 A1* | 5/2007 | Shimizu | ................. G11B 7/005 250/214.1 |
| 2012/0157867 A1 | 6/2012 | Pekonen | |
| 2016/0142017 A1 | 5/2016 | Yoshida et al. | |

FOREIGN PATENT DOCUMENTS

| | | |
|---|---|---|
| EP | 2893873 A3 | 10/2015 |
| WO | WO-2013123358 A1 | 8/2013 |

OTHER PUBLICATIONS

Yang et al., "Configurable Hardware-Efficient Interface Circuit for Multi-Sensor Microsystems", IEEE Sensors, pp. 41-44, Oct. 22-25, 2006.

Huang et al., "A Self-Powered CMOS Reconfigurable Multi-Sensor SoC for Biomedical Applications", IEEE Journal of Solid-State Circuits, vol. 49, Issue 4, pp. 851-866, Apr. 2014.

Helleputte et al., "A 345 µW Multi-Sensor Biomedical SoC With Bio-Impedance, 3-Channel ECG, Motion Artifact Reduction, and Integrated DSP", IEEE Journal of Solid-State Circuits, vol. 50, Issue 1, pp. 230-244, Jan. 2015.

Ha et al., "A Wearable EEG-HEG-HRV Multimodal System with Real-Time tES Monitoring for Mental Health Management", IEEE International Solid-State Circuits Conference, pp. 3, 2015.

Konijnenburg et al., "A Battery-Powered Efficient Multi-Sensor Acquisition System with Simultaneous ECG, BIO-Z, GSR, and PPG", IEEE International Solid-State Circuits Conference, pp. 3, 2016.

Extended European Search Report dated Feb. 23, 2017 for Application No. 16186375.8.

* cited by examiner

RECONFIGURABLE SENSOR CIRCUIT

CROSS-REFERENCE TO RELATED APPLICATIONS

This application claims priority to and the benefit of European Patent Application No. 16186375.8, filed on Aug. 30, 2016, the disclosure of which is incorporated herein by reference in its entirety.

TECHNICAL FIELD

The present inventive concept relates to a reconfigurable sensor circuit, a system and a method for electrical measurements.

BACKGROUND

There is a growing interest in wearable medical devices for measuring multiple types of electrical physiological parameters, for instance electrocardiogram (ECG), bio impedance (BioZ), and electrodermal activity (EDA). Measuring different types of physiological parameters requires development of multi-parameter sensor circuits. There are prior art multi-parameter integrated sensor circuits including multiple types of sensors employing separate readout channels and dedicated circuitry for different parameter types. Although such circuits are able to achieve accurate measurements of multiple parameters, their complexity may render integration more difficult and cause increased production costs.

SUMMARY

An objective of the present inventive concept is to provide an electric circuit which may be used for multiple types of electrical measurements on a measurement object such as a human body and which at least partly reduces the drawbacks of the prior art circuits. Further and alternative objects may be understood from the following.

According to a first aspect of the present inventive concept there is provided a reconfigurable sensor circuit including an input stage comprising a first input terminal and a second input terminal and an amplification stage.

The amplification stage includes: a first amplifier, a second amplifier and first switching circuitry. The first amplifier has a non-inverting input, an inverting input and an output connected to the inverting input of the first amplifier via a first resistor. The second amplifier has a non-inverting input, an inverting input and an output connected to the inverting input of the second amplifier via a second resistor.

The first switching circuitry is adapted to be arranged in a first state, wherein the amplification stage is in a differential amplifier configuration, and in a second state, wherein the amplification stage is in a transimpedance amplifier configuration, wherein, in the differential amplifier configuration, the first amplifier and the second amplifier are together configured as a differential amplifier connected to the first and the second input terminals, and wherein, in the transimpedance amplifier configuration, at least the first amplifier is configured as a transimpedance amplifier connected to the first input terminal.

The amplification stage is hence switchable between the differential and the transimpedance amplifier configurations. Reconfigurability of the sensor circuit is thus enabled.

In the differential amplifier configuration, a voltage difference between the first input terminal and the second input terminal may be amplified and output from the amplification stage. The amplification stage provides a differential voltage output at the output of the first amplifier and the output of the second amplifier. The use of a resistive feedback for the amplifiers makes it possible to amplify both DC and AC signals. The differential amplifier configuration may advantageously be used in a voltage sensing mode of the sensor circuit. As will be further described below the differential amplifier configuration may also advantageously be used in an impedance sensing mode of the sensor circuit.

In the transimpedance amplifier configuration, a current received at the first input terminal may be converted into an amplified output voltage. The amplification stage provides a voltage output at the output of the first amplifier. The differential amplifier configuration may advantageously be used in a current sensing mode of the sensor circuit.

Thus, a same circuit may be used both for voltage sensing and current sensing. This in turn enables various electrical measurements on a measurement object, especially a human body, for instance biosignals, such as potential differences or electrical current, or other electric characteristics such as bioelectrical impedance (BioZ). Depending on what portion of a body the measurement is performed on, a potential difference may be used to acquire an ECG or EEG. A measured electrical resistance may reflect the electrodermal activity (EDA) or galvanic skin response (GSR).

By the design of the amplification stage these electrical measurements may be made via simple skin electrodes connected to input terminals of the circuit. No additional dedicated interface circuitry (such as capacitor arrays or resistive bridges) is needed to interface between the sensor circuit and the skin electrodes.

Hence, overall, the inventive reconfigurable sensor circuit enables multiple types of measurement with an area-efficient circuit which may be produced in a cost efficient manner.

By a sensor circuit is here meant any electronic circuit capable of processing signals received at the input terminals and implementing the various functions of the inventive circuit. The circuit may be implemented in an integrated circuit such as a chipset. The circuit may also be implemented in a field programmable gate array (FPGAs), on a printed circuit board (PCB) with off-the-shelf components, or an application specific integrated circuit (ASICs).

By an input stage or an amplification stage is here meant circuitry, i.e. a circuitry portion of the sensor circuit, being arranged to present the functions and structures associated with said input or amplification stage.

The first input terminal and the second input terminal, as used herein, refers to a part or point of the sensor circuit at which the circuit may be electrically connected to other elements such as measurement electrodes and/or other circuits. An input terminal may for instance be connected to an end part of a lead wire of a skin electrode. The input terminals may be connected directly to a pair of electrodes. The input terminals may also be connected to more than a pair of electrodes via a multiplexer wherein signals from selected pairs of electrodes may be input to the sensor circuit.

Each one of the first and the second amplifier may be any circuitry being able to produce an output signal of increased power or amplitude based on one or more signals input to the amplifier. An amplifier may in addition to the signal inputs and signal output have power supply inputs.

The first and the second amplifiers may preferably each be an operational amplifier. By the output of the first/second amplifier being connected to the inverting input of the first/second amplifier a resistive feedback for the first/second amplifier is formed.

The first switching circuitry may comprise a plurality of independently controllable switches. The switches may be formed by transistors, for instance MOSFETs or BJTs. By controlling the states of the switches, the function of the sensor circuit may be reconfigured. More specifically, the reconfigurable sensor circuit may be controlled to operate in a specific sensing mode, such as for example the above-mentioned voltage sensing mode or the current sensing mode.

A set of one or more switches may be connected between the inverting input of the first amplifier and the inverting input of the second amplifier and being arranged to connect/disconnect the inverting input of the first amplifier to/from the inverting input of the second amplifier.

A set of one or more switches may be connected between the non-inverting input of the first amplifier and the non-inverting input of the second amplifier and being arranged to connect/disconnect the non-inverting input of the first amplifier to/from the non-inverting input of the second amplifier.

A set of one or more switches may be connected between the inputs of the first amplifier and the first input terminal and be arranged to connect a selected one of the inverting and non-inverting input to the first input terminal and disconnect the other one.

A set of switches one or more may be connected between the inputs of the second amplifier and the second input terminal and being arranged to connect a selected one of the inverting and non-inverting input to the second input terminal and disconnect the other one.

According to one embodiment, in the differential amplifier configuration, the non-inverting input of the first amplifier is connected to the first input terminal and the non-inverting input of the second amplifier is connected to the second input terminal, and the inverting input of the first amplifier is connected to the inverting input of the second amplifier via at least one resistor. The first amplifier and the second amplifier are hence configured as a respective non-inverting amplifier with a resistive feedback. The gain of the output is proportional to the ratio between the sum of the resistance of the first and the second resistor and the resistance of the at least one resistor connected between the inverting inputs of the first and the second amplifier.

In the differential amplifier configuration the inverting input of the first amplifier may be disconnected from the first terminal and the inverting input of the second amplifier may be disconnected from the second terminal.

In the differential amplifier configuration the non-inverting input of the first amplifier may be disconnected from the non-inverting input of the second amplifier.

According to one embodiment, also the second amplifier is configured as a transimpedance amplifier in the transimpedance amplifier configuration, the second amplifier being connected to the second input terminal. A current received at the second input terminal may be converted into an amplified output voltage output at the output of the second amplifier. Thereby, either the output of the first amplifier or the second amplifier may be measured. A two-channel current measurement is hence possible.

According to one embodiment, in the transimpedance amplifier configuration, the inverting input of the first amplifier is connected to the first input terminal. The first amplifier is hence configured as a non-inverting amplifier with a resistive feedback. The gain of the output is proportional to the resistance of the first resistor (i.e. the feedback resistor).

Optionally, also the inverting input of the second amplifier may be connected to the second input terminal in the transimpedance amplifier configuration wherein also the second amplifier may be configured as a non-inverting amplifier with a resistive feedback.

In the transimpedance amplifier configuration, the inverting input of the first amplifier may be disconnected from the inverting input of the second amplifier.

In the transimpedance amplifier configuration the non-inverting input of the first amplifier may be disconnected from the first terminal (and optionally the non-inverting input of the second amplifier may be disconnected from the second terminal).

According to one embodiment the sensor circuit further comprises:

an analog-to-digital conversion stage having a first input and a second input, and second switching circuitry adapted to be arranged in a first state wherein the first input of the analog-to-digital conversion stage is connected to the output of the first amplifier and the second input of the analog-to-digital conversion stage is connected to the output of the second amplifier, and in a second state wherein the first input of the analog-to-digital conversion stage is connected to the output of the first amplifier and the second input of the analog-to-digital conversion stage is connected to a voltage reference input (preferably a DC voltage reference).

By an analog-to-digital conversion stage is hereby meant circuitry being able to convert a (continuous) analog signal to a (discrete) digital signal.

By connecting the first input of the analog-to-digital conversion stage to the first output of the amplification stage and the second input of the analog-to-digital conversion stage to the second output of the amplification stage a differential voltage output from the amplification stage may be digitized.

By connecting the first input of the analog-to-digital conversion stage to the first output of the amplification stage and the second input of the analog-to-digital conversion stage to the DC voltage reference input, the difference voltage between the output of the first amplifier and the voltage reference input may be digitized.

The sensor circuit may be arranged to, in a voltage sensing mode and/or in an impedance sensing mode of the sensor circuit (i.e. when the amplification stage is in a differential amplifier configuration), switch the second switching circuitry to the first state.

The sensor circuit may be arranged to, in a current sensing mode (i.e. when the amplification stage is in an transimpedance configuration), switch the second switching circuitry to the second state.

The voltage reference input enables a common mode voltage at the inputs of the first amplifier to be cancelled before the further processing by the analog-to-digital conversion stage. The voltage reference input may advantageously be equal, or approximately equal, to a voltage as output by a DC voltage buffer to be described below. In embodiments where no controlled DC voltage source is present the voltage reference input may be of a voltage corresponding to half of the supply voltage of the first amplifier.

The analog-to-digital conversion stage may include an analog-to-digital converter. The analog-to-digital-converter may be a differential analog-to-digital-converter having a first input and a second input for receiving a differential input signal. The analog-to-digital-converter may have a single-ended output. The output of the analog-to-digital conversion stage may be provided to down-stream digital signal processing components.

The analog-to-digital conversion stage may further include an amplifier arranged to amplify the output signals of the amplification stage, a low pass filter and/or a buffer amplifier. Each of said additional elements may be connected between the second switching circuitry and the analog-to-digital converter.

According to one embodiment the reconfigurable sensor circuit further comprises a DC voltage buffer arranged to output a DC voltage via a terminal of the circuit. The DC voltage may be output via a third terminal of the sensor circuit. Alternatively, the DC voltage may be output via the second input terminal of the sensor circuit.

By a DC voltage buffer is hereby meant a buffer amplifier or a driver having a relatively high input impedance (ideally an infinite input impedance) and a relatively low output impedance (ideally a zero out impedance). That is, the input impedance of the buffer is much higher than the impedance presented to the buffer by a measurement object, and the output impedance of the buffer is much lower than the impedance presented to the buffer output by subsequent circuitry. The DC voltage buffer may for instance be implemented by an operational amplifier arranged with a feedback configuration and having an input connected to a DC voltage. In particular, the operational amplifier may be arranged as a voltage-follower (i.e. a unity gain buffer amplifier).

The DC voltage buffer allows biasing of a measurement object, such as e.g. the body of a user of a wearable device. A potential difference may thereby be induced between the terminal outputting the DC voltage and the input terminals of the input stage.

The DC voltage buffer may be used for biasing of the measuring object in any one of a voltage sensing mode, impedance sensing mode or current sensing mode.

In the transimpedance amplifier configuration (which may be used in a current sensing mode), the potential difference may result in a measurement current received at the first input which may be amplified by the amplification stage.

The sensor circuit may be arranged to control the DC voltage buffer to output the DC voltage in the current sensing mode (wherein the amplification stage is in the transimpedance amplifier configuration) as well as in the voltage sensing mode (wherein the amplification stage is in the differential amplifier configuration.

The reconfigurable sensor circuit may further comprise a controlled DC voltage source switchably connected, via said first switching circuitry, to the non-inverting input of the first amplifier (and optionally also to the non-inverting input of the second amplifier).

By controlled DC voltage source is hereby meant circuitry being able to output a DC voltage of a selectable or controllable signal level. For instance, a controlled DC voltage source may be formed by a digital-to-analog converter arranged to output a voltage selected from a set of discrete voltage levels.

The controlled DC voltage source is advantageous as it allows the first and/or the second amplifier to handle a large input DC offset current without risking saturating (i.e. clipping) the amplifier when in the transimpedance amplifier configuration.

The controlled DC voltage source may be connected to the non-inverting input of the first amplifier (and optionally also to the non-inverting input of the second amplifier) in the transimpedance amplifier configuration and be disconnected from the non-inverting input of the first amplifier (and optionally also from the non-inverting input of the second amplifier) in the differential amplifier configuration.

The sensor circuit may be arranged to control the controlled DC voltage source to output a DC voltage in the current sensing mode (wherein the amplification stage is in the transimpedance amplifier configuration).

The controlled DC voltage source may be arranged to output a DC voltage which is different from a DC voltage output by the DC voltage buffer. The voltage difference between the outputs of the controlled DC voltage source and the DC voltage buffer determines the potential difference induced in the measurement object. As a result, a current, flowing through the resistance between the first terminal and the DC voltage buffer, is inversely proportional to the skin impedance and can be sensed by the sensor circuit in the transimpedance amplifier configuration.

According to one embodiment the circuit further comprises:

a first current source arranged to feed an AC current to a current output terminal, and a second current source arranged to draw an AC current from a current input terminal.

The current output terminal and the current input terminal are preferably different from the first and second input terminals of the input stage. The current output terminal may be arranged to output a current received from the first current source and the current input terminal may be arranged to receive a current output by the current output terminal.

The first current source, the second current source and the associated current terminals may form part of a current stage of the sensor circuit. The current stage enables a well-defined current to be supplied to a measurement object, such as the body of a user, connected between the current output and input terminals. The current supplied to the measurement object will induce a voltage. Simultaneously operating the amplifier stage in the differential amplifier configuration accordingly enables an impedance to be measured on the measurement object (i.e. a bioelectrical impedance, BioZ).

The sensor circuit may accordingly be arranged to control the current stage to drive a current between the current output terminal and the current input terminal and control the amplification stage to operate in the differential amplifier configuration in an impedance sensing mode of the sensor circuit.

The first and the second current source may be AC current sources or DC current sources wherein a separate modulator may be connected between the current sources and the current input/output terminals for up-converting the current to a frequency being suitable for body impedance measurements.

The sensor circuit may further comprise a demodulator connected to the first input terminal and the second input terminal. The demodulator enables an AC voltage to be down-converted to a lower frequency, preferably a DC voltage, thereby reducing the bandwidth requirements on the circuitry following the demodulator. The demodulator may preferably be synchronized to operate at a same frequency as a modulator of the current stage.

The sensor circuit may be arranged to activate the demodulator in the impedance sensing mode and deactivate the demodulator in the voltage sensing mode and the current sensing mode. By "deactivating" the demodulator is hereby meant that the demodulator either is disabled, i.e. controlled to not perform any demodulation on input signals, or that the demodulator is by-passed.

The sensor circuit may further comprise a first high-pass filter switchably connected to the first input terminal and a second high-pass filter switchably connected to the second input terminal. This enables high-pass filtering of the signals received at the first and the second input terminal in a selective manner. By connecting the first high-pass filter to the first input terminal and the second high-pass filter to the second input terminal the sensor circuit may be AC-coupled wherein saturation of the amplification stage by DC currents/voltages in the measurement object may be avoided.

The sensor circuit may be arranged to, in the voltage sensing mode and/or in an impedance sensing mode of the sensor circuit, connect the first and the second high-pass filter to the first and the second input terminal, respectively, wherein the first and the second high-pass filter filters signals received at the first and the second input terminal, respectively.

The sensor circuit may be further arranged to, in the current sensing mode of the sensor circuit, disconnect the first and the second high-pass filter from the first and the second input terminal, respectively.

The first high-pass filter and the second high-pass filter may be formed, respectively, as an RC-filter.

According to a second aspect of the present inventive concept there is provided a system for electrical measurements on a body of a user, comprising the above-described reconfigurable sensor circuit of the first aspect (and any of the above-described embodiments and variations thereof), and a set of skin electrodes connected to the terminals of the circuit. This aspect may generally present the same or corresponding advantages as the former aspect.

The set of skin electrodes may include a first skin electrode connected to the first input terminal of the circuit, a second skin electrode connected to the second input terminal.

The set of skin electrodes may also include a third skin electrode connected to the third terminal of the circuit.

The set of skin electrodes may also include a pair of skin electrodes connected to the current output terminal and to the current input terminal.

By skin electrode is hereby meant a sensing electrode including one or more conducting portions arranged to make galvanic contact with a portion of the skin of a user.

According to a third aspect of the present inventive concept there is provided a method of performing electrical measurements on a body of a user using a sensor circuit in accordance with the above-mentioned first aspect or a system in accordance with the above-mentioned second aspect. This aspect may generally present the same or corresponding advantages as the former aspects.

The method may further comprise:

configuring the circuit in a voltage sensing mode by setting the amplification stage in the differential amplification configuration and switching the second switching circuitry to the first state, and measuring a voltage difference between a first skin electrode connected to the first input terminal of the circuit and a second skin electrode connected to the second input of the circuit.

Further, the first high pass filter may be connected to the first input terminal and the second high pass filter may be connected to the second terminal. Signals received at the first input terminal and the second input terminal may thus be high pass filtered by the first and the second high pass filter.

The method may further comprise:

configuring the circuit in a current sensing mode by setting the amplification stage in the transimpedance amplification configuration, switching the second switching circuitry to the second state; and measuring a current between a first skin electrode connected to the first input terminal of the circuit and a third skin electrode connected to the third terminal of the circuit.

Further, the first high pass filter may be disconnected from the first input terminal and the second high pass filter may be disconnected from the second terminal.

The method may further comprise controlling the output level of the controlled DC voltage source.

The controlled DC voltage source may output (i.e. be controlled to output) a voltage.

The method may further comprise:

configuring the circuit in a voltage sensing mode by setting the amplification stage in the differential amplification configuration and switching the second switching circuitry to the first state, driving a current between the current output terminal and the current input terminal through the body of the user, and measuring an impedance between a first skin electrode connected to the first input terminal of the circuit and a second skin electrode connected to the second input of the circuit.

Further, the first high pass filter may be connected to the first input terminal and the second high pass filter may be connected to the second terminal. Signals received at the first input terminal and the second input terminal may thus be high pass filtered by the first and the second high pass filter.

Further, the demodulator may be activated. Signals received at the first input terminal and the second input terminal may thus be demodulated.

BRIEF DESCRIPTION OF THE DRAWINGS

The above, as well as additional objects, features and advantages of the present inventive concept, will be better understood through the following illustrative and non-limiting detailed description of preferred embodiments of the present inventive concept, with reference to the appended drawings. In the drawings like reference numerals will be used for like elements unless stated otherwise.

DETAILED DESCRIPTION

A reconfigurable sensor circuit 100 (or shorter circuit 100) will first be described with reference to FIG. 1. Three configurations of the reconfigurable sensor circuit, each for a specific type of measurement, will then be described with reference to FIGS. 2-4.

The circuit 100 may be used as an analog front-end of a larger circuit or circuit system for performing multiple types of electrical measurements. Used in such a way, the reconfigurable sensor circuit 100 may supply currents and/or voltages to a measurement object (i.e. the body of a user) and receive/measure currents and/or voltages from the measurement object.

The reconfigurable sensor circuit 100 may be connected to additional circuits and components, outside the scope of the present disclosure, being arranged to perform tasks such as for example post-processing of signals received from the reconfigurable sensor circuit 100, providing a user interface for controlling the reconfigurable sensor circuit 100 and providing power to the reconfigurable sensor circuit 100.

Figure 1:
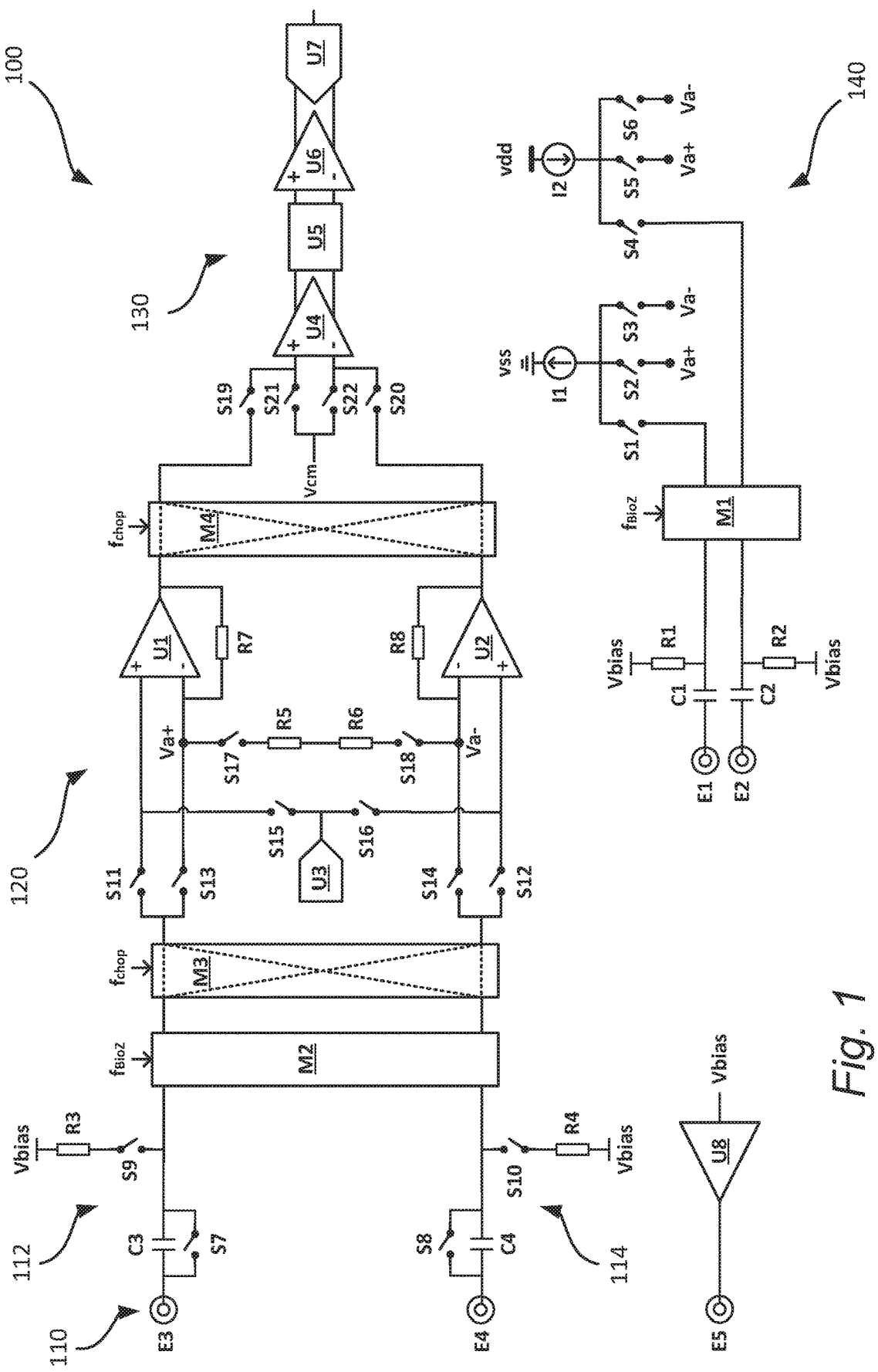
FIG. 1 is a schematic of a reconfigurable sensor circuit.

With reference to FIG. 1, the circuit 100 comprises an input stage 110 comprising a first input terminal E3 and a second input terminal E4. In use of the circuit 100, the input terminals E3, E4 may be connected to a respective portion of the body of the user via a respective skin electrode.

The circuit 100 further comprises a first high-pass filter 112, formed by a resistor R3 and a capacitor C3 and a second high-pass filter 114, formed by a resistor R4 and a capacitor C4. Alternatively, a high pass filter may also be formed by an inductor and a capacitor. The first and second high-pass filter 112, 114 are switchably connected to the first and the second input terminals E3, E4 by means of the switches S7, S9, S8 and S10 respectively. The capacitance values of the capacitors C3 and C4 are preferably equal to each other and may for instance be between 10 pF to 10 µF. The resistance values of the resistors R3 and R4 are preferably equal to each other and may for instance be between 100 kΩ and 100 GΩ.

The circuit 100 further comprises a demodulator M2 connected to the first input terminal E3 and the second input terminal E4. The demodulator M2 has a control input for receiving a frequency input $f_{Bio}Z$ (typically 1 kHz-1 MHz) for setting the frequency of the demodulator M2. The demodulator M2 may be switched between an active state (wherein demodulation is performed) and an inactivate state (wherein no demodulation is performed).

The input stage 110 may further comprise a chopper M3 arranged to modulate the signal at the frequency $f_{chop}$ (typically a few kHz). The chopper M3 may be switched between an active state (wherein the input signals are chopped at the frequency $f_{chop}$) and a inactivate state (wherein no chopping is performed).

The reconfigurable sensor circuit 100 further comprises an amplification stage 120 connected to the input stage 110. The amplification stage 120 is arranged to amplify the signal received from the first input terminal E3 and the signal received from the second input terminal E4.

The amplification stage 120 includes a first amplifier formed by an operational amplifier U1. The first amplifier U1 has a non-inverting input (+), an inverting input (−) and an output. The output of the first amplifier U1 is connected to the inverting input of the first amplifier U1 via a first resistor R7 wherein the first amplifier U1 is arranged with a resistive feedback. The amplification stage 120 further includes a second amplifier formed by an operational amplifier U2. The second amplifier U2 has a non-inverting input (+), an inverting input (−) and an output. The output of the second amplifier U2 is connected to the inverting input of the first amplifier U2 via a second resistor R8 wherein the second amplifier U2 is arranged with a resistive feedback. The first amplifier U1 and the second amplifier U2 may each be powered by a supply voltage Vdd (e.g. supplied via supply terminals, not shown for clarity). The outputs of the first and the second amplifiers U1, U2 form the outputs of the amplification stage 120.

The amplification stage 120 further includes first switching circuitry including switches S11-S18. The non-inverting input and the inverting input of the first amplifier U1 are connectable to the first input terminal E3 via the switches S11 and S13. Accordingly, by controlling the states of the switches S11 and S13 either the non-inverting input or the inverting input of the first amplifier U1 may be connected to the input terminal E3, i.e. be arranged to receive a signal from the first input terminal E3. The non-inverting input and the inverting input of the second amplifier U2 are connectable to the second input terminal E4 via the switches S12 and S14. Accordingly, by controlling the states of the switches S12 and S14 either the non-inverting input or the inverting input of the second amplifier U2 may be connected to the input terminal E4, i.e. be arranged to receive a signal from the second input terminal E4.

The inverting inputs of the first amplifier U1 and the second amplifier U2 are connectable via the switches S17, S18 and the resistors R5, R6. Accordingly, by controlling the states of the switches S17 and S18 the inverting inputs of the first amplifier U1 and the second amplifier U2 may be either disconnected from each other or connected to each other via the resistors R5, R6.

Although in the illustrated circuit 100, two resistors R5, R6 are arranged between the inverting inputs of the first and second amplifiers U1, U2 it is equally possible to arrange less than two or more than two resistors between the inverting inputs. It is also possible to control the connection between the inverting inputs of the first and the second amplifiers U1, U2 by means of a single switch instead of the two switches S17, S18. An advantage of arranging a switch, one or more resistors and a switch in series between the inverting inputs is that the one or more resistors may be completely disconnected from the inverting inputs of the amplifiers U1, U2 in the transimpedance configuration, to be described below.

The resistance values of the resistors R5 and R6 are preferably equal to each other and may for instance be between 1 kΩ and 1 MΩ.

The resistance values of the resistors R7 and R8 are preferably equal to each other and may for instance be between 1 kΩ and 1 MΩ.

The non-inverting inputs of the first amplifier U1 and the second amplifier U2 are connectable via the switches S15, S16. Accordingly, by controlling the states of the switches S15 and S16 the inverting non-inputs of the first amplifier U1 and the second amplifier U2 may be either disconnected from each other or connected to each other.

As shown in FIG. 1, the amplification stage 120 may further include a controlled DC voltage source U3 connectable, via the switches S15, S16, to the non-inverting input of the first amplifier U1 and to the non-inverting input of the second amplifier U2. The output voltage of the controlled DC voltage source is adjustable as will be described below.

The circuit 100 may further comprise a chopper M4 connected to the outputs of the amplification stage 120. The chopper M4 may be arranged to modulate the signal at the frequency $f_{chop}$ (typically a few kHz). The chopper M4 may be switched between an active state (wherein the input signals are chopped at the frequency $f_{chop}$) and a inactivate state (wherein no chopping is performed). If chopping of the input signal is to be performed, M3 and M4 are preferably used in combination.

The circuit 100 further comprises an analog-to-digital conversion stage 130 (or shorter "output stage 130") for digitizing the analog output of the amplification stage 120. The output stage 130 includes a first input and a second input, in the illustrated circuit 100 formed by the inputs of the PGA U4 of the output stage 130.

The output stage 130 is connectable to the outputs of the amplification stage 120 (i.e. via the chopper M4 if present) via second switching circuitry including switches S19, S20. Accordingly, by controlling the state of the switch S19 the output of the first amplifier U1 may be either connected or disconnected from the first input of the output stage 130. By controlling the state of the switch S20 the output of the second amplifier U2 may be either connected or disconnected from the second input of the output stage 130. The second switching circuitry further includes switches S21 and S22 for selectively connecting the first input and the second input, respectively, to a reference voltage input Vcm.

The second switching circuitry S19-S22 may be arranged in a first state wherein the first input of the output stage 130 is connected to the output of the first amplifier U1 and the second input of the output stage 130 is connected to the output of the second amplifier U2, and in a second state wherein the first input of the output stage 130 is connected to the output of the first amplifier U1 and the second input of the output stage 130 is connected to the voltage reference input Vcm.

The output stage 130 includes a programmable gain amplifier (PGA) U4, a low pass filter (LPF) U5, a buffer amplifier U6 and a differential analog-to-digital converter (ADC) U7. The ADC U7 provides a single-ended digital output.

The circuit 100 further includes a DC voltage buffer U8 arranged to output a DC voltage via a terminal E5 of the circuit 100. The DC voltage Vbias which forms an input of the DC voltage buffer U8, and which also forms an input at the resistors R3 and R4, may be provided by a common DC voltage source of the circuit 100 (not shown). The signal level of the DC voltage Vbias may by way of example be in the order of 100 mV-3 V.

The circuit 100 further comprises a current stage 140 including a first current source I2 arranged to feed a current to the current output terminal E2 and a second current source I1 arranged to draw a current from the current input terminal E1. The current source I1 is thus arranged to operate as a current sink.

The current stage 140 further comprises a modulator M1 arranged to up-convert a DC current of the current sources I1, I2 to an AC current at a frequency $f_{BioZ}$ (e.g. for BioZ measurement).

The current stage 140 may further include a respective high-pass filter connected to the current input and output terminals E1, E2. Any DC current remaining after the modulator M1 may thereby be suppressed to protect the user from DC current injection.

The circuit 100 can be operated in different modes for the purpose of supporting different types of measurements. A number of different modes of operation of the circuit 100 will now be discussed with reference to FIGS. 2-4. The circuit diagrams shown in FIGS. 2-4 all structurally illustrates the circuit 100 described above, i.e. the one illustrated in FIG. 1. For clarity, circuitry not in use for a specific mode of operation may be omitted.

The modes of operation will be described with reference to a system for electrical measurements on a body of a user, the system comprising the circuit 100 and a set of skin electrodes (not shown).

The set of skin electrodes may be of a conventional type and may include a first skin electrode connected to the first input terminal E3 of the circuit 100, a second skin electrode connected to the second input terminal E4 of the circuit 100, a third skin electrode connected to the third terminal E5 of the circuit 100, and a pair of skin electrodes connected to the current output terminal and current input terminal E1, E2 of the current stage 140.

The circuit 100 may operate in accordance with a voltage sensing mode, an impedance sensing mode and a current sensing mode. The system may include controller circuitry (not shown) for controlling the circuit 100 in accordance with a selected one of the measurement modes. The controller circuitry may form part of the circuit 100 or form a separate circuit connected to the circuit 100. The controller circuitry may be arranged to output control signals for controlling the states of the switches S1-S22 of the circuit 100. The controller circuitry may be arranged to output control signals for controlling the modulator M1 and the demodulator M2. The controller circuitry may be arranged to output control signals for controlling the choppers M3 and M4. The controller circuitry may be arranged to output control signals for controlling the voltage sources U3. The controller circuitry may be arranged to output control signals for controlling the current source block 140.

Figure 2:
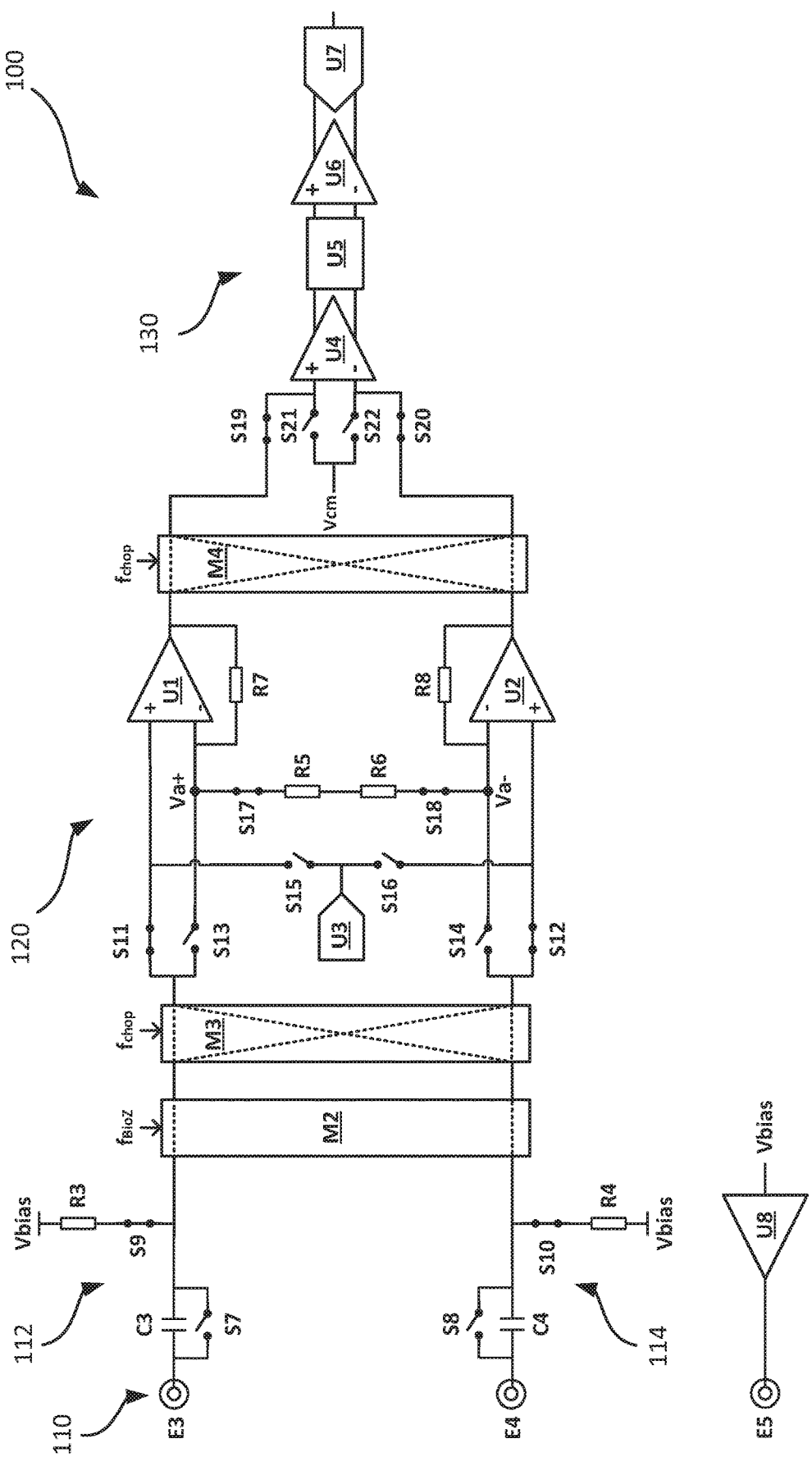
FIG. 2 illustrates the reconfigurable sensor circuit in a voltage sensing mode.

FIG. 2 illustrates the circuit 100 configured in a voltage sensing mode. The voltage sensing mode may be used for measuring a voltage or potential difference between the first input terminal E3 and the second input terminal E4. The first input terminal E3 may be connected to the first skin electrode and the second input terminal E4 may be connected to the second skin electrode. By arranging the first and the second skin electrodes on and in contact with a respective portion of the skin of a human user a potential difference between said portions may be measured by the circuit 100. By arranging the first and the second skin electrodes on appropriate portions of the chest, the circuit 100 may be used for measuring an ECG. By arranging the first and the second skin electrodes on appropriate portions of the head, the circuit 100 may be used for measuring an EEG. The output terminal E5 may be connected to the third skin electrode arranged in contact with a third skin portion for providing biasing of the measurement object.

As shown in FIG. 2, the switches S7 and S8 are open and the switches S9 and S10 are closed wherein the first and second high pass filters 112, 114 are connected to the first and the second input terminals E3 and E4, respectively. Signals received at the first and the second input terminals E3, E4 will accordingly be high-pass filtered. The biasing voltage Vbias applied to the resistors R3 and R4 may be selected to bias the amplifiers U1, U2 into roughly the middle of their linear operating region.

The DC voltage buffer U8 may apply a DC bias to the user, thereby avoiding floating input and reducing noise pickup. Optionally, if R3 and R4 have a comparably high resistance the switches S7 and S8 may be closed the DC voltage buffer U8 would not be needed for biasing since the user then would be biased via E3 and E4 instead.

The demodulator M2 is in an inactive state wherein no demodulation of the input signals is performed.

The choppers M3 and M4 may be active or inactive depending on whether noise levels so requires.

The amplification stage 120 is switched to a differential amplification configuration. The switches S11 and S12 are closed wherein the non-inverting inputs of the first amplifier U1 and the second amplifier U2 are connected to the first input terminal E3 and the second input terminal E4, respectively. The switches S13 and S14 are open wherein the inverting inputs of the first amplifier U1 and the second amplifier U2 are disconnected from the first input terminal E3 and the second input terminal E4, respectively. The switches S15 and S16 are open wherein the non-inverting inputs of the first amplifier U1 and the second amplifier U2 are disconnected from each other. The switches S17 and S18 are closed wherein the inverting inputs of the first amplifier U1 and the second amplifier U2 are connected to each other via the resistors R5 and R6.

In the differential amplification configuration the voltage difference between the voltage $V_{U1}$ output by the first amplifier U1 and the voltage $V_{U2}$ output by the second amplifier U2 is given by (assuming the amplifiers U1 and U2 are ideal operational amplifiers):

$$V_{U1} - V_{U2} = \Delta V \left(1 + \frac{R7 + R8}{R5 + R6}\right),$$

where ΔV represents the voltage difference between the non-inverting inputs of the first and the second amplifiers U1, U2 and R5-R8 represents the resistance values of the correspondingly labeled resistors.

The switches S19 and S20 of the second switching circuitry are closed wherein the outputs of the amplification stage 120 are connected to the inputs of the output stage 130. The switches S21, S22 of the second switching circuitry are open.

The differential output of the amplification stage 120 is converted to a digital signal by the ADC U7, following optional amplification by the PGA U4 and low pass filtering by the LPF U4.

Figure 3:
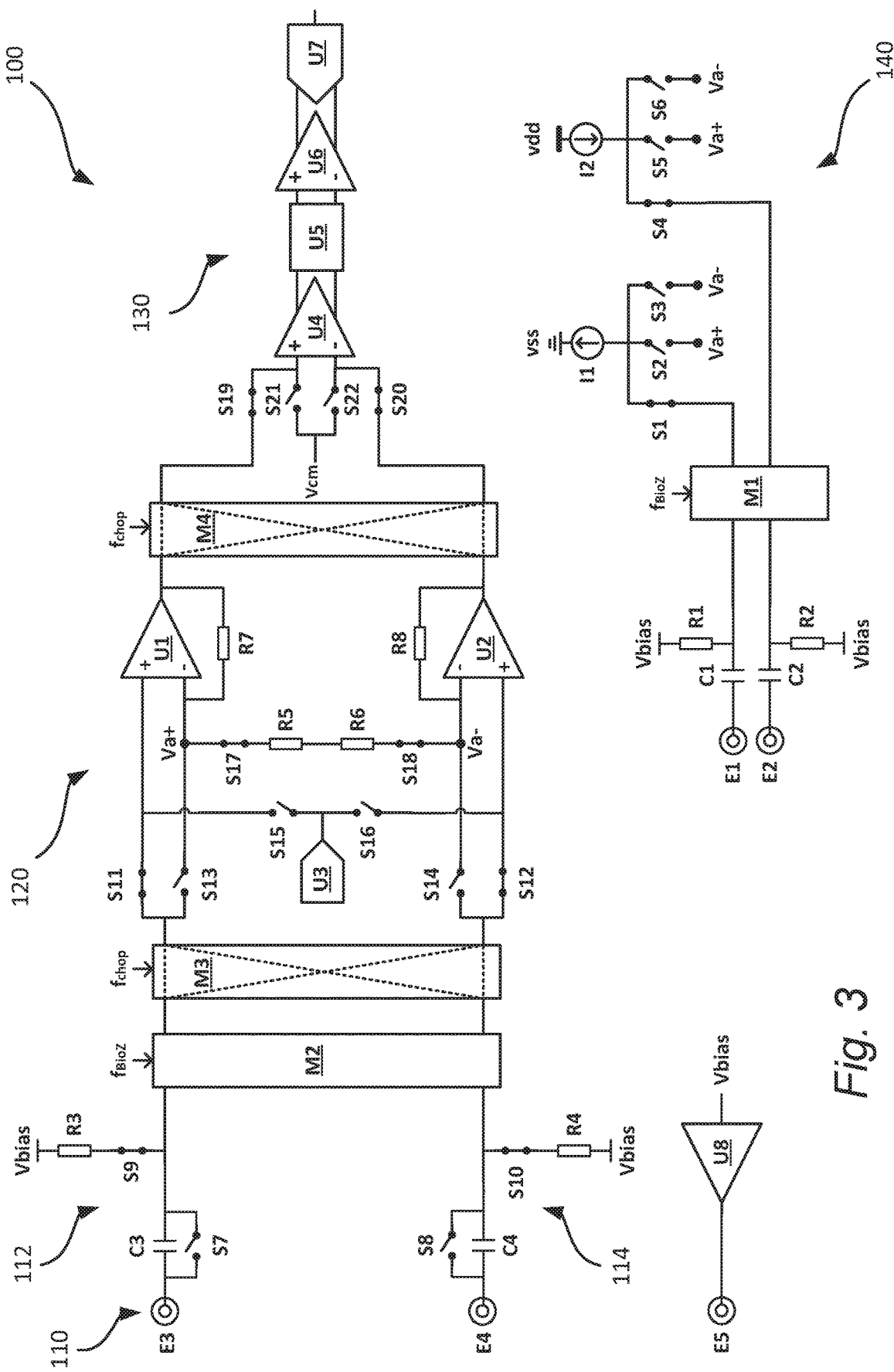
FIG. 3 illustrates the reconfigurable sensor circuit in an impedance sensing mode.

FIG. 3 illustrates the circuit 100 configured in an impedance sensing mode. The impedance sensing mode may be used for measuring an impedance between the first input terminal E3 and the second input terminal E4. The first input terminal E3 may be connected to the first skin electrode and the second input terminal E4 may be connected to the second skin electrode. The output terminal E5 may be connected to the third skin electrode. The current input and output terminals E1, E2 of the current stage 140 may be connected to the further pair of skin electrodes. The pair of skin electrodes may be arranged on and in contact with a respective portion of the skin of a human user. The current stage 140 may inject an AC current into the human user via the pair of skin electrodes. By arranging the first and the second skin electrodes on and in contact with a respective portion of the skin of the user, preferably between the pair of skin electrodes connected to the current stage 140, a potential difference induced by the injected AC current between said portions may be measured by the circuit 100. Accordingly, a body impedance or BioZ of the user may be measured.

As shown in FIG. 3, the switches S1 and S4 of the current source block 140 are closed wherein the current sources I1 and I2 are connected to the current input and output terminals E1, E2. The modulator M1 is active and up-converts the DC currents of the current sources I1 and I2 to AC currents at the frequency $f_{BioZ}$. For the purpose of measuring body impedance, $f_{BioZ}$ is preferably in the range 1 kHz to 1 MHz. The modulator M1 may be arranged to operate at a fixed frequency or the modulator M1 may be arranged to operate at a variable frequency. The frequency $f_{BioZ}$ of the modulator M1 may be controlled by the controller circuitry providing a control signal to the modulator M1.

The DC voltage buffer U8 may apply a DC bias to the user, thereby avoiding floating input and reducing noise pickup.

The first and second high pass filters 112, 114 are connected to the first and the second input terminals E3 and E4, respectively, as described with reference to the voltage sensing mode above.

The demodulator M2 is in an active state. The demodulator M2 is controlled to operate at the same frequency $f_{BioZ}$ as the modulator M1 wherein AC input signals are down-converted to DC signals. Similar to the modulator M1, the demodulator M2 may be controlled by the controller circuitry.

The choppers M3 and M4 may be active or inactive depending on whether noise levels so requires.

The amplification stage 120 is switched to a differential amplification configuration, as described with reference to the voltage sensing mode above.

The switches S19-S22 are switched in a same manner as in the voltage sensing mode described above wherein the outputs of the amplification stage 120 are connected to the inputs of the output stage 130.

The differential output of the amplification stage 120 is converted to a digital signal by the ADC U7, following optional amplification by the PGA U4 and low pass filtering by the LPF U4.

Based on the digitized output of the LPF U4 and knowledge of the current driven by the current source 140 the impedance may be determined using techniques which per se are well-known in the art.

Figure 4:
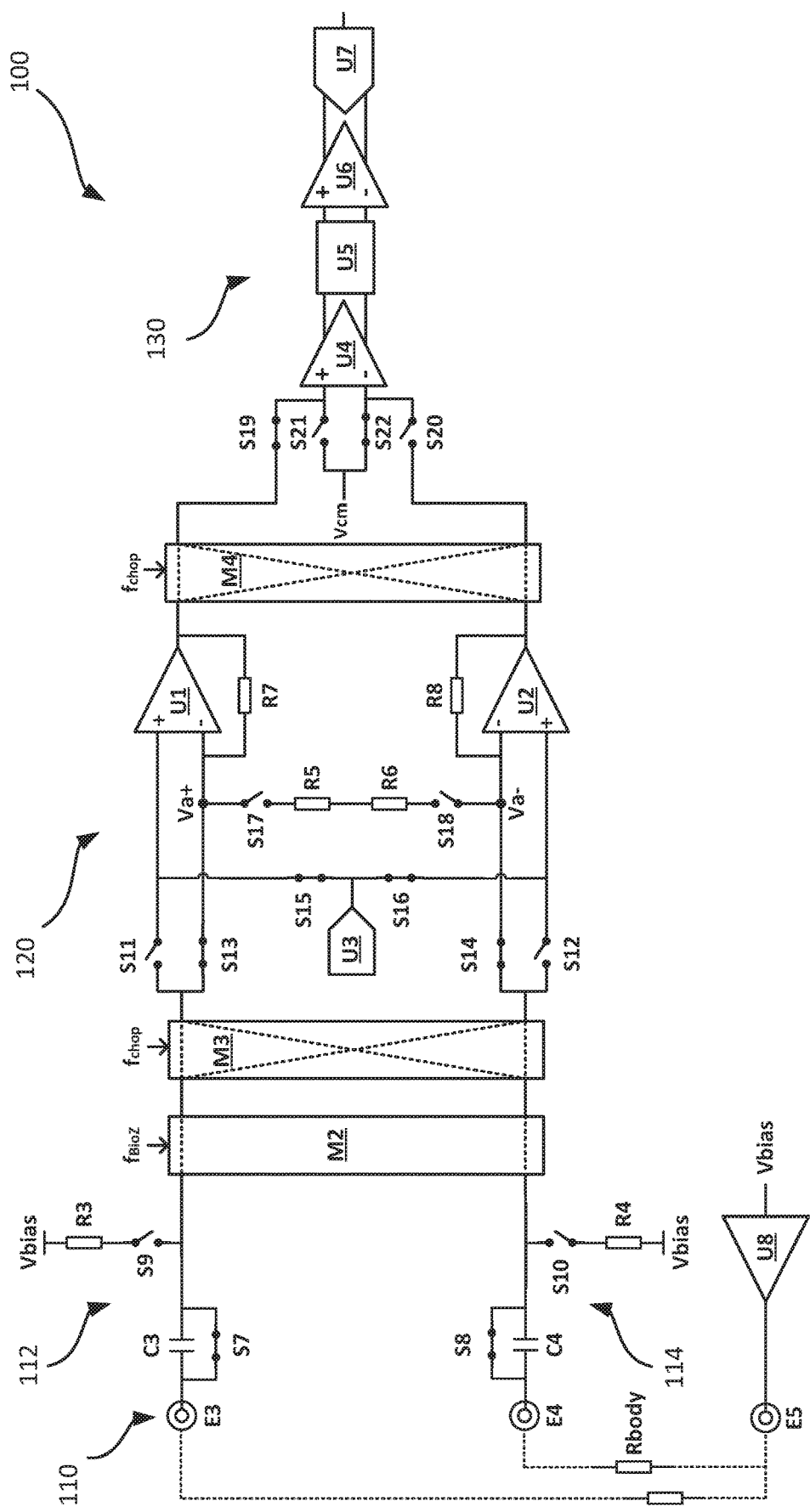
FIG. 4 illustrates the reconfigurable sensor circuit in a current sensing mode.

FIG. 4 illustrates the circuit 100 configured in a current sensing mode. The current sensing mode may be used for measuring a current received at the first input terminal E3 or the second input terminal E4. The first input terminal E3 may be connected to the first skin electrode and the second input terminal E4 may be connected to the second skin electrode. The output terminal E5 may be connected to the third skin electrode. By arranging the first, the second and the third skin electrodes on and in contact with a respective portion of the skin of a human user a current flowing through the body of the user, between the third skin electrode and either of the first or second skin electrodes may be measured by the circuit 100. In FIG. 4, a schematic circuit model including the portion of the body traversed by the current is represented by the dashed lines and the resistors Rbody. By measuring the current, an electrodermal activity (EDA) or galvanic skin response (GSR) of the user may be measured.

As shown in FIG. 4, the switches S7 and S8 are closed and the switches S9 and S10 are open wherein the first and second high pass filters 112, 114 are disconnected from the first and the second input terminals E3 and E4, respectively. Signals received at the first and the second input terminals E3, E4 will accordingly bypass the first and the second high pass filters 112, 114.

The demodulator M2 is in an inactive state wherein no demodulation of the input signals is performed.

The choppers M3 and M4 may be active or inactive depending on whether noise levels so requires.

The amplification stage 120 is switched to a transimpedance amplifier configuration. The switches S11 and S12 are open wherein the non-inverting inputs of the first amplifier U1 and the second amplifier U2 are disconnected from the first input terminal E3 and the second input terminal E4, respectively. The switches S13 and S14 are closed wherein the inverting inputs of the first amplifier U1 and the second amplifier U2 are connected to the first input terminal E3 and the second input terminal E4, respectively. The switches S17 and S18 are open wherein the inverting inputs of the first amplifier U1 and the second amplifier U2 are disconnected from each other. The switches S15 and S16 are closed wherein the non-inverting inputs of the first amplifier U1 and the second amplifier U2 are connected to each other. The output voltage of the controlled DC voltage source U3 is input to the non-inverting inputs of the first amplifier U1 and the second amplifier U2.

The output voltage of the controlled DC voltage source U3 is adjustable. For instance, the output voltage may be adjustable between Vcm±400 mV in steps of one or a few tens of mV. The output voltage of the controlled DC voltage source U3 may be controlled by the controller circuitry such as to counter a DC offset of the current input at the first terminal E1 or second terminal E2. Thereby saturation of the first or the second amplifier U1, U2 may be avoided, and the programmable voltage enables a wide measurement range.

In the transimpedance amplifier configuration the voltage $V_{U1}$ output by the first amplifier U1 is given by (assuming the amplifier U1 is an ideal operational amplifier):

$$V_{U1} = V_{DAC} + R7\left(\frac{Vbia - V_{DAC}}{Rbody}\right),$$

where $V_{DAC}$ represents the output of the controlled DC voltage source U3, Vbias represents the output of voltage buffer U8 and R7 represents the resistance value of the correspondingly labeled resistor.

The switch S19 of the second switching circuitry is closed wherein the output of first amplifier U1 is connected to the first input of the output stage 130. The switch S22 of the second switching circuitry is closed wherein the second input of the output stage 130 is connected to the reference voltage Vcm. The switches S21 and S22 are open.

By controlling the output of the controlled DC voltage source U3 based on Vcm the common mode voltage at the inverting and non-inverting inputs of the first amplifier U1 may be reduced from the input to the output stage 130.

The output of the amplification stage 120 is converted to a digital signal by the ADC U7, following optional amplification by the PGA U4 and low pass filtering by the LPF U4.

As may be understood from FIG. 4, the output voltage $V_{U2}$ of the second amplifier U2 presents an equivalent dependency on the current received by the second input terminal E4. Accordingly, it is equally possible to provide the output of $V_{U2}$ of the second amplifier U2 to the output stage 130 by closing the switches S20 and S21 and opening the switches S19 and S22. A time-duplexed two-channel current measurement is hence possible. Accordingly, the controller circuitry may in a time-division manner change the states of the switches S19-S22 to switch between measurement of the input signal received at the first input terminal E3 and the input signal received at the second input terminal E4.

For controlling the magnitude of the input DC current to the amplifier U1, the current stage 140 (not shown in FIG. 4) may also be used by closing the switches S2, S3 or S5 and S6 wherein the outputs of the current sources I1 and I2 are supplied to the inverting inputs of U1 and U2, as indicated by the Va+ and Va− labels in FIG. 3. Saturation of the amplifiers U1, U2 due to large input DC current may thereby be avoided. The switches S2, S3 may be closed if the input DC current is of positive polarity and the switches S5, S6 may be closed if the input DC current is of negative polarity.

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A reconfigurable sensor circuit comprising:
an input stage including a first input terminal and a second input terminal, and
an amplification stage including:
a first amplifier having a non-inverting input, an inverting input, and an output, the output of the first amplifier connected to the inverting input of the first amplifier via a first resistor,
a second amplifier having a non-inverting input, an inverting input, and an output, the output of the second amplifier connected to the inverting input of the second amplifier via a second resistor, and
first switching circuitry adapted to be arranged in a first state, wherein the amplification stage is in a differential amplifier configuration, and in a second state, wherein the amplification stage is in a transimpedance amplifier configuration,
wherein, in the differential amplifier configuration, the first amplifier and the second amplifier are together configured as a differential amplifier connected to the first and the second input terminals, wherein the non-inverting input of the first amplifier is connected to the first input terminal and the non-inverting input of the second amplifier is connected to the second input terminal, and the inverting input of the first amplifier is connected to the inverting input of the second amplifier via at least one resistor, and
wherein, in the transimpedance amplifier configuration, at least the first amplifier is configured as a transimpedance amplifier connected to the first input terminal.

2. A circuit according to claim 1, wherein, in the transimpedance amplifier configuration, the inverting input of the first amplifier is connected to the first input terminal.

3. A circuit according to claim 1, further comprising:
an analog-to-digital conversion stage having a first input and a second input, and
second switching circuitry adapted to be arranged in a first state wherein the first input of the analog-to-digital conversion stage is connected to the output of the first amplifier and the second input of the analog-to-digital conversion stage is connected to the output of the second amplifier, and in a second state wherein the first input of the analog-to-digital conversion stage is connected to the output of the first amplifier and the second input of the analog-to-digital conversion stage is connected to a voltage reference input.

4. A circuit according to claim 1, further comprising a DC voltage buffer arranged to output a DC voltage via a terminal of the circuit.

5. A circuit according to claim 1, further comprising a controlled DC voltage source switchably connected, via said first switching circuitry, to the non-inverting input of the first amplifier.

6. A circuit according to claim 1, further comprising:
a first current source arranged to feed an AC current to a current output terminal, and
a second current source arranged to draw an AC current from a current input terminal.

7. A circuit according to claim 1, further comprising a demodulator connected to the first input terminal and the second input terminal.

8. A circuit according to claim 1, further comprising a first high-pass filter switchably connected to the first input terminal and a second high-pass filter switchably connected to the second input terminal.

9. A system for electrical measurements on a body of a user, comprising:
a circuit according to claim 1;
a set of skin electrodes connected to the terminals of the circuit.

10. A system according to claim 9, wherein said set of skin electrodes includes a first skin electrode connected to the first input terminal of the circuit, a second skin electrode connected to the second input terminal of the circuit, a third skin electrode connected to the third terminal of the circuit, and a pair of skin electrodes connected to the current output terminal and current input terminal of the circuit.

11. A method of performing electrical measurements on a body of a user using a system for electrical measurements on a body of a user, the system comprising:
 a reconfigurable sensor circuit comprising:
  an input stage including a first input terminal and a second input terminal, and
  an amplification stage including:
   a first amplifier having a non-inverting input, an inverting input, and an output, the output of the first amplifier connected to the inverting input of the first amplifier via a first resistor,
   a second amplifier having a non-inverting input, an inverting input, and an output, the output of the second amplifier connected to the inverting input of the second amplifier via a second resistor, and
  first switching circuitry adapted to be arranged in a first state, wherein the amplification stage is in a differential amplifier configuration, and in a second state, wherein the amplification stage is in a transimpedance amplifier configuration,
   wherein, in the differential amplifier configuration, the first amplifier and the second amplifier are together configured as a differential amplifier connected to the first and the second input terminals, wherein the non-inverting input of the first amplifier is connected to the first input terminal and the non-inverting input of the second amplifier is connected to the second input terminal, and the inverting input of the first amplifier is connected to the inverting input of the second amplifier via at least one resistor, and
   wherein, in the transimpedance amplifier configuration, at least the first amplifier is configured as a transimpedance amplifier connected to the first input terminal; and the system further comprising a set of skin electrodes connected to the terminals of the circuit.

12. A method in accordance with claim 11, further comprising:
 configuring the circuit in a voltage sensing mode by setting the amplification stage in the differential amplification configuration and switching the second switching circuitry to the first state, and
 measuring a voltage difference between a first skin electrode connected to the first input terminal of the circuit and a second skin electrode connected to the second input of the circuit.

13. A method in accordance with claim 11, further comprising
 configuring the circuit in a current sensing mode by setting the amplification stage in the transimpedance amplification configuration, switching the second switching circuitry to the second state; and
 measuring a current between a first skin electrode connected to the first input terminal of the circuit and a third skin electrode connected to the third terminal of the circuit.

14. A method in accordance with claim 11, further comprising: configuring the circuit in an impedance sensing mode by setting the amplification stage in the differential amplification configuration and switching the second switching circuitry to the first state,
 driving a current between the current output terminal and the current input terminal through the body of the user, and
 measuring an impedance between a first skin electrode connected to the first input terminal of the circuit and a second skin electrode connected to the second input of the circuit.

* * * * *